United States Patent
Bertha et al.

(10) Patent No.: US 6,861,225 B1
(45) Date of Patent: Mar. 1, 2005

(54) METHOD AND REAGENT KIT FOR DETERMINING ACTIVITY OF 5-NUCLEOTIDASE

(76) Inventors: András Bertha, Mária tér 4., H-1011 Budapest (HU); István Tulok, Dózsa György u.23/b, H-2013 Pomáz (HU)

( * ) Notice: Subject to any disclaimer, the term of this patent is extended or adjusted under 35 U.S.C. 154(b) by 0 days.

(21) Appl. No.: 10/296,136
(22) PCT Filed: Jul. 3, 2000
(86) PCT No.: PCT/HU00/00069
§ 371 (c)(1), (2), (4) Date: Nov. 21, 2002
(87) PCT Pub. No.: WO01/90403
PCT Pub. Date: Nov. 29, 2001

(51) Int. Cl.[7] ............................ C12Q 1/68; G01N 33/53
(52) U.S. Cl. .............................. 435/6; 435/7.1; 435/7.2
(58) Field of Search ............................. 435/6, 7.1, 7.2

(56) References Cited

PUBLICATIONS

Paglia et al. The Journal of Biological Chemistry, vol. 250, No. 20, pp. 7973–7979, 1975.*

El–Aaser, Abdel–basset Anwer, et al., "Simultaneous Determination of 5'–Nucleotidase and Alkaline Phosphatase Activities in Serum," *Z. Klin. Chem. Klin. Biochem.*, vol. 13, No. 10, pp. 453–459 (1975).

Parthasarathi, K., et al., "Effect of Spike Disease on the 5'- and 3'–Nucleotidase Activities in Sandal Plants," *Experientia*, vol. 37, No. 5, pp. 448–449 (1981).

Wood, Raymond John, et al., "Colorimetric Determination of Serum 5'–Nucleotidase without Deproteinization," *Clin. Chem.*, vol. 27, No. 3, pp. 464–465 (1981).

Fioretti, E., et al., "Spectrophotometric Assays for 5'–Nucleotidase, Using IMP, GMP and CMP as Substrates," *The Italian Journal of Biochemistry*, vol. 21, No. 3, pp. 103–112 (May–Jun. 1972).

Bodansky, Oscar, et al., "5'–Nucleotidase," *Advances in Clinical Chemistry*, vol 11, pp. 277–328 (1968).

* cited by examiner

Primary Examiner—Jezia Riley
(74) Attorney, Agent, or Firm—Speckman Law Group PLLC; Janet Sleath; Victor N. King

(57) ABSTRACT

The invention relates to a method for determining activity of 5'-nucleotidase, in which a biological sample is incubated in a manner and under conditions known per se with a nucleotide pentose monophosphate as substrate, the liberated inorganic phosphate is converted into a colored complex by treating it with ammonium molybdate and a reducing agent, color intensity is measured by a known method, and from the measured value the activity of 5'-nucle-otidase or the amount of inorganic phosphate liberated within unit time, as a figure proportional to the activity of 5'-nucleotidase, is calculated with a known calculation and/or with the aid of a calibration curve. According to the invention 5'-AMP, 5'-CMP, 5'-UMP, 5'-GMP, 5'-IMP and 5'-TMP are used as nucleotide pentose monophosphates, and measurement is performed on all of these six substrates. The invention also relates to a reagent kit for performing the above method.

6 Claims, No Drawings

METHOD AND REAGENT KIT FOR DETERMINING ACTIVITY OF 5-NUCLEOTIDASE

The invention relates to a method for determining the activity of 5'-nucleotidase (5'-ribonucleotide phosphohydrolase) in body fluids, tissue preparates and/or cell elements. The invention also relates to a reagent kit usable in the method according to the invention.

FIELD OF THE INVENTION

Of the metabolic disturbances which are coupled with, incidental to and maintaining factors of malignant processes, too, changes in nucleotide metabolism play an outstanding role. This explains why influencing of DNA/RNA synthesis and of the nucleic acid-nucleotide metabolism closely connected to these processes is one of the main goals of the interventions used in tumour therapy.

BACKGROUND OF THE INVENTION

Examination of nucleic acid-nucleotide metabolic processes has an outstanding importance in detecting tumorous processes and in distinguishing benignant and malignant processes from one another. Examination of the changes in nucleic acid metabolic processes is indispensible from the aspects of monitoring tumour therapy, too, since in the overwhelming majority of chemotherapeutical treatments the therapeutic effect appears in artificially provoked disturbances of the nucleic acid-nucleotide metabolism and in artificial damaging of DNA synthesis. These artificially provoked changes are decisive factors of the effectiveness of tumour therapy, however, they are also responsible for basic damages of healthy cells and disturbances of cell and organ functions.

Under routine conditions the determination of the activity of 5'-nucleotidase (5'-ribonucleotide phosphohydrolase), an enzyme detected by Reis (Reis, J.: Über die spezifische Phosphatase der Nerwengewebe: Enzymologia 2, 110–115/1937/), is one of the most appropriate methods. This enzyme catalyzes solely the hydrolysis of nucleotide pentose monophosphates (5'-AMP, 5'-CMP, 5'-UMP, 5'-GMP, 5'-IMOP, 5'-TMP, dAMP, dCMP, dUMP, etc.), yielding nucleotides and inorganic phosphate (Bodansky, O., Schwartz, M. K.: 5'-Nucleotidase; Adv. Clin. Chem. 11, 277–327/1968/), and can be regarded as one of the most sensitive plasm membrane markers. Determination of the activity of 5'-nucleotidase is used both for clinical purposes and in experimental tests; in the former instance measurment is performed usually on non-haemolysed serum and/or on a haemolysate, whereas in the latter instance measurement can be performed on body fluids, on tissue preparates (e.g. on plasm membranes) and/or on cell elements (e.g. on microsomes, cytoplasms, lysosomes) (see: Solyom, A., Trans., E. G.: Enzyme Markers in Characterization of Isolated Plasma Membranes: Enzyme 13, 329–372/1972/).

As 5'-nucleotidase is an enzyme which splits specifically nucleotide pentose monophosphates, a widely applied method for determining the activity of 5'-nucleotidase is to incubate the biological sample with a nucleotide pentose monophosphate substrate and then, after adding an appropriate colour developing reagent, to determine by colorimetry (spectrophotometry) the amount of inorganic phosphate liberated within unit time upon the effect of the enzyme. If the biological sample to be examined also comprises components which interfere with 5'-nucleotidase enzyme (for blood or serum such a component is alkaline phosphatase, for lysosome membrane such components are the other sugar phosphates), incubation is performed in the presence of an inhibitor capable of inhibiting their effects. As colour developing reagent ammonium molybdate is applied in the presence of a reducing agent, which is usually stannous chloride optionally together with a hydrazine salt orascorbic acid, which reacts with the inorganic phosphate to form an intense blue complex. Considering that ammonium molybdate precipitates the proteins present in the biological sample, proteins are either removed before performing the colour reaction, or proteins are kept in solution by adding an appropriate solubilizing agent to the mixture. To our recent knowledge, this latter is one of the most up-to-date calorimetric methods. Utilizing this method, the sample requirement of the determination can even be reduced to some hundredth milliliters, and the accuracy of the assay can be increased considerably. Determination of the activity of 5'-nucleotidase on the above principle is disclosed in detail, among others, in the following papers and in further references cited therein: J. Clin. Chem. Clin. Biochem. 7, 18–25 (1969), 13,453–459 (1975), 15, 715–718 (1977), 18, 781–788 (1980); Clin. Chem. 23, 2311–2323 (1977)127, 464–465 (1981); Adv. Clin. Chem. 11, 277–332 (1968).

A common feature of all routine methods applied before to determine the activity of 5'-nucleotidase on the above basis for diagnostic or general experimental purposes is that enzyme activity has been measured only on a single substrate. As substrate, most frequently adenosine-5'-monophosphate (5'-AMP), less frequently cytidine-5'-monophosphate (5'-CMP) or inositol-5'-monophosphate, or -in haemo-lysates-uridine-5'-monophosphate (5'-UMP) is applied.

SUMMARY OF THE INVENTION

In our examinations performed to detect malignant processes and to monitor the efficiacy of tumour therapy the activity of 5'-nucleotidase in one and the same biological sample has been measured in parallel on six different substrates, i.e. on adenosine-5'-monophosphate (5'-AMP), cytidine-5'-monophosphate (5'-CMP), uridine-5'-monophage (5'-UMP), guanosine-5'-monophosphate (5'-GMP), inositol-5'-monophosphate (5'-IMP) and thymidine-5'-monophosphate (5'-TMP). The activity of non-specific phosphatase in the biological sample has been measured on β-glycerophosphate substrate, and this was taken as correction. As it was expectable on the basis of the references cited above, we have observed that although the 5'-nucleotidase activity values measured on different nucleotide pentose monophosphates quantitatively differ from one another, on healthy and sick individuals there is a strict correlation between the activity values measured on different substratres. This is because under physiological conditions a dynamic equilibrium state of nucleic acid-nucleotide metabolism processes exists in the serum as a common metabolic pool. Again, as it follows from the literature, we have observed that the 5'-nucleotidase activity values measured on the above six substrates in sera of healthy and sick individuals differ from one another to such an extent which cannot be attributed to the differences in the chemical natures of the substrates, but result from physiologic processes. However, we have found, unexpectedly, that the above strict correlation changes upon therapy, and considerable differences appear on the basis whether the therapy has exerted its effects on the purine metabolism, on the pyrimidine metabolism, or on the thymidine metabolism. Thus, based on the results of activity measurements performed on the above six different substrates, it can be decided whether the applied therapy is effective, whether it exerts its effects on the field intended to be influenced, and whether it induces undesirable cell damages or not. This recognition forms the basis of our invention.

Based on the above, the invention relates to a method for diagnosing the existence of a malignant process and/or for monitoring the results of a therapy applied in its treatment by determining 5'-nucleotidase activity, in which a biological sample is incubated in a manner and under conditions known per se with a nucleotide pentose monophosphate as substrate, the liberated inorganic phosphate is converted into a coloured complex by treating it with ammonium molybdate and a reducing agent, colour intensity is measured by a known method, and from the measured value the activity of 5'-nucleotidase or the amount of inorganic phosphate liberated within unit time, as a figure proportional to the activity of 5'-nucleotidase, is calculated with a known calculation and/or with the ais of a calibration curve. According to the invention 5'-AMP, 5'-CMP, 5-UMP, 5'-GMP, 5'-IMP and 5'-TMP are used as nucleotide pentose monophosphates, the measurement is performed on all of these six substrates, and the obtained results are compared with on another and with control valves.

Since upon a chemotherapeutic treatment well observable changes in the activity of 5'-nucleotidase appear on all the six different substrates even after a short period (24 hours), a well-founded decision can be brought on the maintenance, modification or termination of therapy within a shorter period of time and with less ambiguities. Here we remark, for the purpose of comparison, that a change which may serve as a basis for decision can be observed with most of the tumour markers only after about 1 week of treatment.

DETAILED DESCRIPTION OF THE INVENTION

When the activity of 5'-nucleotidase is measured in parallel on all of the above six substrates and the results are summarized, much more reliable diagnosis can be set up on the condition of the individual and on the occurrence of liver and bone processes than it could be obtained when the measurement would be performed only on a single substrate. This may provide a valuable assistance to the early recognition of malignant processes.

Based on the consequential interconnections of biochemical processes, activity measurements of 5'-nucleotidase on the above six substrates may replace enzyme activity determinations which are less frequently used in experimental and clinical practice, since they are much more complicated and are difficult to perform as a routine test, if at all. These replacement or substitution possibilities are e.g. as follows: 5'-CMP nucleotidase→cytidine kinase→cytidine deaminase→cytidine triphosphate synthetase; 5'-GMP nucleotidase→guanosine deaminase, 5'-IMP nucleotidase→IMP dehydrogenase; 5'-TMP nucleotidase→thymidine kinase↔thymidine synthetase.

Of the reactants required in the measurements, of the reaction conditions and of the method of calculation detailed information can be found in the literature, among others in the papers cited above. As an example, in the following we give the composition of a reagent system applicable for measurements without protein removal, which proved to be particularly preferred, and also describe how it should be used in measurements performed on serum samples, together with the method of calculation, without, however, limiting the usability of the method of the invention to the reagent system and to the conditions disclosed below.

The reagents to be used are as follows:

(1) Buffer/Activator Solution:

75–400 mmoles/l of TRIS, 5.0–10.0 mmoles/l of $MgCl_2$ or 2.0–5.0 mmoles/l of $MnCl_2$, 1.0–5.0 mmoles/l of KCl; the pH of the solution being adjusted to 9–9.5 with a 3–6 M aqueous HCl solution.

(2) Inhibitor:

An inhibitor should be used only when the biological sample comprises a substance which interferes with the determination of the activity of 5'-nucleotidase. For blood and serum such a substance is alkaline phosphatase, which can be inhibited with a solution containing 10–20 g/l of L-cysteine or L-glycine or an equivalent amount of a L-cysteine- or L-glycine-salt, or 50–250 mg/l of Concavalin A, the solvent being the buffer described above. When the measurements are performed on lysosome membranes, a solution of 5–50 mmoles/l of L(+)-tartarate in the above buffer is used to inhibit the sugar phosphates present.

(3) Substrates:

As substrates 5'-AMP, 5'-CMP, 5'-UMP, 5'-GMP, 5'-IMP and 5'-TMP are used as 1–10 mmolar solutions in demineralized water. β-Glycerophosphate or disodium-phenylphosphate should also be used as substrate in a solution of the same concentration. The latter two substrates are two known substrates of the determination of nonspecific phosphatase activity; this activity should also be determined in order to determine accurately the activity of 5'-nucleotidase.

(4) Protein Solubilizing Reagent:

Neat (concentrated) formic acid or propionic acid of the highest purity grade.

(5) Stabilizing Reagent:

A 1:9 to 4:6 v/v mixture of glycerol and water, or a 0.5–5 w/w % aqueous sorbitol solution, or a 0.25–2.5 w/w % aqueous mannitol solution, or a 1:2 to 1:1 v/v mixture of n-propanol and water.

It is advisable to dissolve a small amount (0.001–0.01 w/w %) of sodium azide in the stabilizing reagent in order to increase its storability.

(6) Colour Reagent:

A 5–10 g/l solution of ammonium molybdate in demineralized water.

(7) Reducing Solution:

A 1–5 g/l solution of $SnCl_2$ in 1 M aqueous hydrochloric acid, or a 1–5 g/l solution of ascorbic acid in demineralized water.

(8) Phosphorous Standard Solution:

A 1.61 mmol/l solution of inorganic phosphate, which is diluted in series.

Measurement is performed as follows:

An assay reagent for determining the amount of inorganic phosphate is prepared by admixing the protein solubilizing reagent in a volume/volume ratio of 4:1 to 1:1 with the aqueous glycerol solution, or 3:1 to 1:1 with the aqueous sorbitol solution, or 5:1 to 1:2 with the aqueous mannitol solution, or 7:1 to 4:1 with the aqueous n-propanol solution, and 15–25% by volume, related to the total volume of the final mixture, of the colour reagent is added to the resulting mixture.

The components listed in the first five lines of Table 1 are admixed with one another in the ratios as indicated in the Table, and the resulting mixture is incubated at 37° C. for 60 minutes. Thereafter the further components listed in Table 1 are added to the mixture, the resulting mixture is stirred, then allowed to stand for 15 minutes, and thereafter the absorbance of the solution is measured at 620–720 nm. The column in Table 1 with the heading "5'-ND+ALP" relates to measurements where the activity of 5'-nucleotidase is measured together with the activity of alkaline phosphatase (i.e. no inhibitor is used), whereas the column with the heading "5'-ND" relates to measurements performed in the presence of an inhibitor for alkaline phosphatase. The activity of nonspecific phosphatase appears in the results of both measurements. Nonspecific phospatase activity is determined separately on β-glycerophosphate substrate in the presence of an inhibitor; the resulting value is subtracted from the previous ones to obtain the activity of 5'-nucleotidase+alkaline phosphatase or the activity of 5'-nucleotidase, respectively.

Calculation is performed as follows:

(a) Calculation of extinction differences (ΔE values):

$$\beta\text{-glycerophosphate: } E_{sample} - E_{blind} = \Delta E_{\beta\text{-glycerophosphate}}$$

$$\text{other substrates: } E_{sample} - E_{sample\ blind} = \Delta E_{\text{5'-AMP, 5'-CMP, 5'-UMP, 5'-GMP, 5'-TMP, 5'-IMP}}$$

$$\text{standard: } E_{standard} - E_{reagent\ blind} = \Delta E_{standard}$$

(b) Calculation of enzyme activities on the basis of the above ΔE values:

$$\text{Activity, } U/l \text{ of sample} = \frac{\text{Sample } \Delta E}{\text{Standard } \Delta E} \times \text{Standard cc.} \times K,$$

wherein
Standard cc. is the concentration of the standard, and K is a constant calculated from the following formula:

$$\frac{\text{total incubated volume, ml} \times 1000}{\text{incubation period,}}$$
$$\text{min.} \times \text{sample volume, ml} \times \text{couvette thickness}$$

(c) Calculation of individual enzyme activities or combined activities from the above activity data:

Nonspecific phosphatase activity=the activity measured on β-glycerophosphate 5'-Nucleotidase activities measured on different nucleotide pentose monophosphates=5-ND activity−nonspecific phosphatase activity 5'-Nucleotidase+alkaline phosphatase activity=5'-ND+ALP−nonspecific phosphatase activity Alkaline phosphatase activity=5'-ND+ALP−5-ND−nonspecific phosphatase activity If the biological sample is other than serum, the measurement is performed in the same manner, with the difference that sometimes no inhibitor is necessary, or other inhibitor is used. The calculations are also performed as given above.

TABLE 1

| Solution | 5'-ND + ALP | 5'-ND | Sample blind | Standard | Reagent blind |
|---|---|---|---|---|---|
| Buffer/activator | 0.125 ml | 0.125 ml | 0.125 ml | — | — |
| De-mineralized water | 0.075 ml | 0.050 ml | 0.075 ml | — | — |
| Inhibitor | — | 0.025 ml | — | — | — |
| Sample (serum) | 0.025 ml | 0.025 ml | — | — | — |
| Substrate | 0.025 ml | 0.025 ml | — | — | — |
| Assay reagent | 0.750 ml | 0.750 ml | 0.750 ml | 0.750 ml | 0.750 ml |
| De-mineralized water | — | — | — | 0.125 ml | 0.250 ml |
| Sample (serum) | — | — | 0.025 ml | — | — |
| Substrate | — | — | 0.025 ml | — | — |

TABLE 1-continued

| Solution | 5'-ND + ALP | 5'-ND | Sample blind | Standard | Reagent blind |
|---|---|---|---|---|---|
| Standard | — | — | — | 0.125 ml | — |
| Reducing solution | 0.125 ml | 0.125 ml | 0.125 ml | 0.125 ml | 0.125 ml |

From the 5'-nucleotidase activity values obtained on the individual substrates in the above series of measurements the following biological conclusions can be drawn:

Decision on a status: The figure obtained upon summarizing the six measured activity values denotes a disease-free state up to 54–65 U/l, provided that at the same time alkaline phosphatase activity is 10–25 U/l. If alkaline phosphatase activity is above 50 U/l and at the same time the sum of 5'-nucleotidase activity values is 54–65 U/l, an indication of malignant bone processes arises. If the sum of 5'-nucleotidase activities is above 70 U/l, this is a sure indication of sick state. If at the same time alkaline phosphatase activity is above 35 U/l, this is a sure indication of the presence of liver damages. For malignant liver tumours both the sum of 5'-nucleotidase activity values and the alkaline phosphatase activity are 4–10 times higher than the normal values.

Evaluation of a therapy: A change in activity measured on 5'-AMP, 5'-GMP and 5'-IMP substrates indicates that the tumour therapy has intervened in the purine metabolism, whereas a change in activity measured on 5'-CMP, 5'-UMP and 5'-TMP substrates indicates an intervention in the pyrimidine metabolism. Unchanged values indicate that the therapy is useless. A decrease in activity indicates always that the therapy exerted a beneficial intervention in the processes. It occurs in numerous cases that upon the applied chemotherapy the decrease in 5'-nucleotidase activities is so pronounced that both the activities measured separately on the individual substrates and the sum of these activities are lower than 10 U/l, even more, sometimes negative figures can also be obtained for 5-nucleotidase activities. This arises from the fact that the therapy attacks nucleotide metabolism, but does not influence nonspecific phosphatase activity values; a negative activity value is obtained when a higher nonspecific phosphatase activity value should be subtracted from a lower 5'-ND activity value. When 5'-nucleotidase activity values are lower than those obtained for healthy controls, this is already an indication of cytotoxic damages of healthy cells with rapid nucleotide metabolisms (primarily of intestinal mucosa, bone marrow and erythrocites), particularly when such a change occurs at all 5'-nucleotidase activities measured on all the six substrates. In such instances therapy should be modified or stopped.

The invention also relates to a reagent kit usable for the method of the invention, which comprises 5'-AMP, 5'-CMP, 5'-UMP, 5'-GMP, 5'-IMP and 5'-TMP as substrates beside the conventional components of a reagent kit applicable to determine 5'-nucleotidase activity via forming an inorganic phosphate, converting the resulting phosphate into a coloured complex and measuring colour intensity by photometry.

The conventional components of the reagent kit may be those utilized for the known methods, e.g. for those disclosed in the publications cited above. A preferred reagent kit may comprise the following conventional components:

buffer, protein solubilizing reagent, stabilizing reagent, colour reagent, reducing agent, phosphorous standard, further, if required, inhibitor, and/or a substrate other than a nucleotide pentose monophosphate (such as β-glycerophosphate).

Preferred representatives of the above conventional components are those listed above at the exemplified description of the method of the invention. The reagent kit may comprise the conventional components either as solutions with the above-indicated concentrations, or as more concentrated solutions to be diluted before use, or as neat chemicals.

In the following, as an example, results of 5'-nucleotidase activity measurements performed on serum samples are given, together with the conclusions which can be drawn therefrom. The amounts of the individual substances and the assay conditions were always those as given in Table 1. The accurate compositions of the individual reagents used in the measurements were as follows:

(1) Buffer/activator solution: 75.0 mmoles/l of TRIS.HCl, 5.0 mmoles/l of $MgCl_2$, 5.0 mmoles/l of KCl: pH: 9.3.

(2) Inhibitor: 0.29 g of L-cysteine HCl dissolved in 20.0 ml of the buffer/activator solution.

(3) Substrates: 8.0 mmoles/l solutions of 5'-AMP, 5'-CMP, 5'-UMP, 5'-GMP, 5'-IMP, 5'-TMP and β-glycerophosphate in demineralized water.

(4) Protein solubilizing reagent: Neat (concentrated) formic acid of the highest analytical purity grade.

(5) Stabilizing reagent: 300 ml of glycerol of the highest analytical purity grade+700 ml of demineralized water+0.05 g of $NaN_3$.

(6) Colour reagent: 8.0 g/l solution of ammonium molybdate in demineralized water.

(7) Reducing solution: 0.20 g of $SnCl_2$ dissolved in 100 ml of 1.0 M aqueous hydrochloric acid.

(8) Phosphorous standard solution: "Dyalab"[R] type inorganic phosphate solution with a concentration of 1.61 mmoles/l (for further thousandfol dilution)

Assay reagent: 200 ml of component (4) admixed with 200 ml of component (5) and 100 ml of component (6).

Measurements were performed for the following cases:

On healthy individuals and on individuals with clinically diagnostized tumours before treatment. The results are listed in Table 2.

For monitoring CMF (cyclophosphamide-methoxtrexate-5-fluorouracyl) therapy of patients with mammalian tumours after surgery. The results are listed in Tables 4 and 5.

For monitoring methotrexate (a folic acid-antagonizing agent) therapy of patients with osteosarcoma. The results are listed in Table 7.

For simplifying purposes In Table 2 and in all of the subsequent tables only the symbols of the respective substrates were indicated; these refer, however, always to the 5'-nucleotidase activity values measured on the given substrates.

From the data of Table 2 it appears that, with the exception of lymphoma+bone manifestation, 5'-nucleotidase activity values measured on the six substrates increased considerably on patients suffering from the examined malignomes in comparison to the healthy control values. The sum of 5'-nucleotidase activity values (Σ5'-ND) showed the most pronounced increase for lung tumours and or lymphomas coupled with liver manifestations. The increase of alkaline phosphatase activity, compared to the change in 5'-nucleotidase activity, was the most pronounced for lymphomas coupled with bone manifestations.

TABLE 2

| | Enzyme activity, U/l ± standard deviation | | | | | | | |
|---|---|---|---|---|---|---|---|---|
| Groups tested | 5'-AMP | 5'-CMP | 5'-UMP | 5'-GMP | 5'-IMP | 5'-TMP | Σ5'-ND | Alk. ph. |
| Healthy control | 6.5 | 10.1 | 8.4 | 4.1 | 3.3 | 8.5 | 40.9 | 13.2 |
| n = 157 | ±1.2 | ±2.2 | ±1.6 | ±1.1 | ±0.9 | ±1.6 | ±1.43 | ±4.4 |
| Mammalian carcinoma | 23.45 | 50.92 | 34.8 | 13.76 | 10.6 | 27.87 | 161.4 | 45.7 |
| n = 341 | ±4.1 | ±9.8 | ±4.7 | ±4.3 | ±3.3 | ±5.8 | ±5.33 | ±7.8 |
| Ovarian carcinoma | 47.56 | 95.87 | 67.1 | 33.2 | 13.7 | 30.4 | 287.8 | 65.5 |
| n = 189 | ±7.8 | ±9.1 | ±6.9 | ±4.4 | ±3.5 | ±6.1 | ±6.3 | ±11.2 |
| Thyroid carcinoma | 34.66 | 70.3 | 45.4 | 22.3 | 17.8 | 45.1 | 235.56 | 57.6 |
| n = 76 | ±7.2 | ±9.7 | ±5.9 | ±4.4 | ±5.2 | ±9.5 | ±6.98 | ±12.3 |
| non-Hodgkin lymphoma | 23.5 | 46.8 | 34.5 | 11.6 | 9.11 | 18.6 | 144.11 | 23.4 |
| n = 45 | ±5.6 | ±8.4 | ±5.1 | ±6.3 | ±2.2 | ±3.2 | ±5.13 | ±4.4 |
| Hodgkin disease | 34.6 | 80.6 | 57.5 | 21.2 | 10.7 | 15.5 | 220.1 | 43.3 |
| n = 36 | ±3.9 | ±12.7 | ±7.4 | ±5.2 | ±1.9 | ±3.2 | ±5.71 | ±6.2 |
| Melanoma malignans | 10.8 | 23.7 | 15.8 | 5.7 | 8.8 | 23.2 | 88.01 | 41.3 |
| n = 1567 | ±2.3 | ±3.8 | ±2.9 | ±0.89 | ±1.5 | ±4.3 | ±2.61 | ±6.8 |
| Lung tumour | 67.7 | 123.4 | 78.3 | 34 | 23 | 34 | 360.4 | 62.2 |
| n = 76 | ±13.4 | ±19.4 | ±13.5 | ±5.9 | ±3.9 | ±4.5 | ±10.15 | ±11.2 |
| Lymphoma + bone | 9.2 | 10.8 | 8.2 | 5.4 | 3.3 | 9.8 | 45.8 | 167.6 |

TABLE 2-continued

| Groups tested | Enzyme activity, U/l ± standard deviation | | | | | | | |
|---|---|---|---|---|---|---|---|---|
| | 5'-AMP | 5'-CMP | 5'-UMP | 5'-GMP | 5'-IMP | 5'-TMP | Σ5'-ND | Alk. ph. |
| manifestation, n = 23 | ±2.3 | ±1.7 | ±1.1 | ±0.9 | ±0.2 | ±1.8 | ±1.33 | ±23 |
| Lymphoma + liver manifestation, n = 76 | 89.7 ±19 | 189.7 ±23 | 102.6 ±31 | 45.8 ±12 | 34.9 ±8.9 | 34.6 ±4.6 | 497.3 ±16.41 | 56.7 ±11.2 |

As it appears from the data of Table 3, strict correlations can be found between the 5'-nucleotidase activity values-belonging to the individual substrates, as well as between the activity measured on 5'-AMP and the activity measured on β-glycerophosphate which indicates nonspecific phosphatase activity, both for the patients suffering from the examined malignomes and being before treatment and for the healthy controls.

TABLE 3

| Correlation pairs | Correlation |
|---|---|
| 5'-AMP 5'-CMP | 0.9943 |
| 5'-AMP 5'-UMP | 0.9728 |
| 5'-AMP 5'-GMP | 0.9234 |
| 5'-AMP 5'-IMP | 0.9656 |
| 5'-AMP 5'-TMP | 0.9878 |
| 5'-CMP 5'-UMP | 0.9456 |
| 5'-CMP 5'-GMP | 0.9678 |
| 5'-CMP 5'-IMP | 0.9489 |
| 5'-CMP 5'-TMP | 0.8978 |
| 5'-UMP 5'-GMP | 0.8989 |
| 5'-UMP 5'-IMP | 0.9323 |
| 5'-UMP 5'-TMP | 0.9562 |
| 5'-GMP 5'-IMP | 0.8978 |

TABLE 3-continued

| Correlation pairs | Correlation |
|---|---|
| 5'-GMP 5'-TMP | 0.9545 |
| 5'-AMP β-glycerophosphate | 0.8978 |

The results of the measurements applied to monitor the therapy of patients subjected to mammalian tumourectomy and then to chemotherapy are given in Tables 4 and 5. Table 4 summarizes the data of successful cases, whereas Table 5 summarizes the data of cases resistant to CMF-therapy. Data obtained after therapy change are also given in Table 5. In therapy change the patients were subjected to Cis-platin therapy, and 5'-nucleotidase activities were measured 1 day after the first treatment (*) and 1 day after terminating the therapy (**). In all other cases measurements were performed 24 hours after the actual chemotherapeutic treatment. For comparison purposes, values measured on healthy controls are also given.

TABLE 4

| | 5'-nucleotidase activity, U/l ± standard deviation | | | | | | |
|---|---|---|---|---|---|---|---|
| | 5'-AMP | 5'-CMP | 5'-UMP | 5'-GMP | 5'-IMP | 5'-TMP | Σ5'-ND |
| Healthy control | 6.5 ±1.2 | 10.1 ±2.2 | 8.4 ±1.6 | 4.1 ±1.1 | 3.3 ±0.9 | 8.5 ±1.6 | 40.9 ±1.43 |
| Sick, before CMF | 29.4 ±3.7 | 34.7 ±7.8 | 11.8 ±3.4 | 7.9 ±1.8 | 7.6 ±1.1 | 19.8 ±3.7 | 112.2 ±3.5 |
| After 1 series of CMF | 11.6 ±2.1 | 3.4 ±0.9 | 4.6 ±1.2 | 2.3 ±0.8 | 3.2 ±0.9 | 4.5 ±1.4 | 29.6 ±1.2 |
| After 3 series of CMF | 3.4 ±1.1 | 2.3 ±0.9 | 2.1 ±0.9 | −2.4 ±0.1 | −2.8 ±0.8 | 1.1 ±0.03 | 1.28 ±0.63 |
| After 6 series of CMF | 0.7 ±0.04 | −1.7 ±0.3 | 2.2 ±0.7 | −3.3 ±0.8 | 1.1 ±0.1 | −3.4 ±0.7 | −4.4 ±0.44 |

From the data the following conclusions can be drawn: 5'-nucleotidase activities measured on 5'-CMP, 5'-GMP, 5'-IMP and 5'-TMP substrates decreased considerably already after the first series of CMF treatments. After the third series of CMF treatments considerably great decreases could be observed in 5'-nucleotidase activities measured on 5'-AMP, 5'-GMP and 5'-IMP substrates. After the sixth series of CMF treatments considerable decreases appeared in 5'-nucleotidase activities measured on 5'-AMP, 5'-CMP, 5'-GMP and 5'-IMP substrates. For drug combinations the effect exerted on the point of attack is difficult to define, owing to the different points of attack of the individual components. Thus in such instances a comparison to the status before treatment serves as guidance. The measured data show that the drug combination applied exerts its therapeutic effect in two phases, via the consequences exerted on the purine and pyrimidine metabolism processes.

TABLE 6

| Correlation pairs | Correlation | |
|---|---|---|
| | Before chemotherapy | After chemotherapy |
| 5'-AMP 5'-CMP | 0.9856 | 0.6767 |
| 5'-AMP 5'-UMP | 0.8997 | 0.4561 |
| 5'-AMP 5'-GMP | 0.7845 | 0.3267 |
| 5'-AMP 5'-IMP | 0.8967 | 0.4519 |
| 5'-AMP 5'-TMP | 0.7897 | 0.4687 |
| 5'-CMP 5'-UMP | 0.9897 | 0.5639 |
| 5'-CMP 5'-GMP | 0.7868 | 0.2345 |
| 5'-CMP 5'-IMP | 0.8887 | 0.2689 |
| 5'-CMP 5'-TMP | 0.6767 | 0.1123 |
| 5'-UMP 5'-GMP | 0.8978 | 0.3493 |
| 5'-UMP 5'-IMP | 0.8889 | 0.0567 |
| 5'-UMP 5'-TMP | 0.8992 | 0.3635 |
| 5'-GMP 5'-IMP | 0.9981 | 0.4684 |
| 5'-GMP 5'-TMP | 0.9767 | 0.4781 |
| 5'-IMP 5'-TMP | 0.8898 | 0.4356 |

TABLE 5

| | 5'-nucleotidase activity, U/l ± standard deviation | | | | | | |
|---|---|---|---|---|---|---|---|
| | 5'-AMP | 5'-CMP | 5'-UMP | 5'-GMP | 5'-IMP | 5'-TMP | Σ5'-ND |
| Healthy control | 6.5 | 10.1 | 8.4 | 4.1 | 3.3 | 8.5 | 40.9 |
| | ±1.2 | ±2.2 | ±1.6 | ±1.1 | ±0.9 | ±1.6 | ±1.43 |
| Sick, before CMF | 39.6 | 72.4 | 45.8 | 23.7 | 18.9 | 24.7 | 225.11 |
| | ±8.67 | ±11.3 | ±10.9 | ±7.8 | ±3.5 | ±6.2 | ±8.05 |
| After 1 series of CMF | 26.7 | 68.9 | 40.2 | 19.8 | 16.4 | 21.1 | 193.1 |
| | ±5.3 | ±10.2 | ±9.9 | ±6.9 | ±4.6 | ±5.2 | ±7.01 |
| After Cis-platin (*) | 20.3 | 43.2 | 26.5 | 4.2 | 2.3 | 8.9 | 115.4 |
| | ±3.4 | ±8.1 | ±5.7 | ±1.1 | ±0.9 | ±1.8 | ±3.5 |
| After Cis-platin (**) | 4.1 | 3.6 | 4.4 | −1.6 | 1.1 | 1.2 | 12.8 |
| | ±1.3 | ±0.9 | ±1.5 | ±0.8 | ±0.6 | ±0.3 | ±1.2 |

After an ineffective CMF treatment no significant changes could be observed in the 5'-nucleotidase activities measured on the individual substrates; therefore therapy was continued with Cis-platin. On the basis of the results we have observed that significant changes in 5'-nucleotidase activities belonging to the individual substrates occurred already in the first stage of Cis-platin treatment (24 hours after treatment; marked by * in the Table); considerable decreases could be observed primarily on substrates participating in the purine metabolism. The values measured on the first day following termination of Cis-platin treatment (marked by ** in the Table) indicate that the changes in purine metabolism are followed in time by changes in pirimidine metabolism, with the remark that the changes in the two metabolic processes are superimposed. Our tests revealed the ineffectiveness of CMF therapy already 5 days before the measurement with diagnostic tumor marker CA 15-3 (which also indicated ineffectiveness), thus the patients could be saved of a five days' superfluous CMF treatment.

The success and effectivity of therapy is also reflexted by the fact that the initial strict correlation between the 5'-nucleotidase activity values measured on different substrates changes. Correlation values calculated after a successful therapy are listed in Table 6 below, where the pre-therapy values are also given for comparison purposes.

The data of Table 6 show that the initial strict correlation between the 5'-nucleotidase activities measured on the different substrates has ceased, which also reflects that measurements on different substrates enable one to separately detect and evaluate the individual biological processes proceeding during therapy.

Determination of 5'-nucleotidase activity with the six above substrates provides irreplaceably useful pieces of information in those cases, too, when chemotherapy has no direct influence on the nucleotide metabolism. A good example of this situation is the methothrexate treatment of osteosarcomatic patients. Methothrexate is a substance with folic acid antagonizing effect, it has no direct effect on the nucleotide metabolism, thus every change in nucleotide metabolism which occurs upon methothrexate treatment indicates a de novo nucleotide synthesis, i.e. a damaging of healthy cells. Any damages occurring incidentally upon treatment have steadily serious consequences; such a consequence may be e.g. a reduction of cellular and humoral immunity, which may also induce formation of a second tumour.

Changes in 5'-nucleotidase activities measured on osteosarcomatic patients treated with 12.0 g doses of methothrexate are summarized in Table 7.

From the data of Table 7 the following conclusions can be drawn:

The results of 5'-nucleotidase activity determinations performed on the six substrates applied to examine the changes in pyrimidine and purine metabolism show that, in the first period, the treatment affects the pyrimidine metabolism. The differences between the two metabolic pathways are particularly pronounced 44 hours after treatment. It also appears from the data of Table 7 that considerable differences can be observed between the individual substrates even within one and the same metabolic pathway. This phenomenon is unequivocally due to the differences between the biochemical functions of the individual substrates. Upon monitoring the therapy according to the method of the invention it becomes possible to stop or change the therapy before the detected disturbances would lead to more serious changes as late consequences.

TABLE 7

| | 5'-nucleotidase activity, U/I | | | | | |
|---|---|---|---|---|---|---|
| | Pyrimidine metabolism | | | Purine metabolism | | |
| Time | 5'-AMP | 5'-CMP | 5'-UMP | 5'-GMP | 5'-IMP | 5'-TMP |
| 0 min. | −8.39 | 5.33 | 5.05 | 3.34 | 3.77 | 1.56 |
| 15 min. | −3.12 | 2.21 | 0.14 | 0.57 | −0.2 | −6.75 |
| 30 min. | −11.87 | −2.19 | 1.92 | −2.19 | 2.98 | −6.89 |
| 1 hour | −5.05 | 2.41 | 1.2 | −2.1 | 1.34 | −1.01 |
| 2 hours | −4.84 | 5.97 | 2.77 | 2.84 | −3.49 | −2.49 |
| 3 hours | −0.5 | 8.6 | 4.05 | 7.61 | 5.68 | 2.41 |
| 4 hours | −3.63 | 6.76 | 4.19 | 0.92 | −0.28 | −3.98 |
| 6 hours | −10.32 | −1.63 | −1.85 | −5.48 | −2.7 | −3.7 |
| 12 hours | −1.71 | −0.15 | 1.48 | 1.98 | 3.69 | −4.49 |
| 21 hours | −2.56 | 6.04 | 5.83 | −0.99 | 0.35 | −4.84 |
| 44 hours | 31.38 | 4.69 | 7.89 | 1.99 | −12.95 | −9.46 |
| 69 hours | 7.96 | 18.42 | 14.93 | 13.16 | 13.01 | 8.6 |
| 90 hours | 6.83 | 13.09 | 15.16 | 3.49 | 10.1 | 3.63 |
| 162 hours | −12.6 | 6.97 | 29.53 | −6.33 | −1.99 | −1.35 |
| 186 hours | 1.41 | 7.53 | 12.16 | 14.94 | 6.54 | 0.35 |
| 210 hours | 5.76 | 4.48 | 7.39 | 3.91 | −3.91 | 0.92 |
| 234 hours | 8.61 | 3.48 | 10.88 | 8.68 | 5.47 | 6.11 |
| 258 hours | 3.99 | 2.42 | 2.64 | 0.22 | 0.43 | −5.82 |
| 330 hours | 9.25 | 7.47 | 2.99 | 8.46 | 10.53 | −2.7 |
| 358 hours | 9.67 | 5.47 | 4.9 | 5.97 | −2.28 | 2.56 |
| 402 hours | 5.18 | 8.03 | 9.59 | 8.24 | 6.04 | 5.4 |

Although in the above the method and reagent kit according to the invention have been disclosed in connection with diagnostic use, the scope of the invention is not limited to this type of use. The method and reagent kit can also be utilized with excellent results for research purposes, e.g. to detect the mechanisms of certain malignant processes, to test known or new anti-cancer agents and to examine the mechanism of their effects.

What we claim is:

1. A method for diagnosing the existence of a malignant process and/or for monitoring results of a therapy applied in its treatment by determining 5'-ribonucleotide phosphohydrolase activity, wherein a biological sample is incubated with a nucleotide pentose monophosphate as substrate, the liberated inorganic phosphate is converted into a colored complex by treating it with ammonium molybdate and a reducing agent, color intensity is measured, and from the measured value the activity of 5'-ribonucleotide phosphohydrolase or the amount of inorganic phosphate liberated within unit time, as a figure proportional to the activity of 5'-ribonucleotide phosphohydrolase is calculated, wherein 5'-AMP, 5'-CMP, 5'-UMP, 5-GMP, 5'-IMP and 5'-TMP are used as nucleotide pentose monophosphates, the measurement is performed on all of these six substrates, and the obtained results are compared with one another and with control values.

2. The method of claim 1, wherein the biological sample is incubated with the substrate in a buffered medium optionally in the presence of an inhibitor, and then, over ammonium molybdate and reducing agent, a protein solubilizing reagent and a stabilizing reagent are also added to the incubated mixture.

3. The method of claim 1, wherein the nucleotide pentose monophosphate substrates are used as aqueous solutions with concentrations of 1–10 mmoles/l.

4. The method of claim 1, wherein whole blood, serum or a haemolysate is used as biological sample, and incubation with the substrate is performed both in the presence and in the absence of an alkaline phosphatase inhibitor.

5. A reagent kit for performing a method of claim 1, comprising 5'-AMP, 5'-CMP, 5'-UMP, 5'-GMP, 5'-IMP and 5'-TMP as substrates together with conventional components of a reagent kit applicable to determine 5'-ribonucleotide phosphohydrolase activity via forming an inorganic phosphate, converting the resulting phosphate into a colored complex and measuring color intensity by photometry.

6. The reagent kit of claim 5, wherein the conventional components is selected from the group consisting of: a buffer, a protein solubilizing reagent, a stabilizing reagent, a color reagent, a phosphorous standard, and optionally an inhibitor and/or a substrate other than a nucleotide pentose monophosphate.

* * * * *